(12) United States Patent
Hwang et al.

(10) Patent No.: US 7,777,086 B2
(45) Date of Patent: Aug. 17, 2010

(54) PRODUCTION OF ALKYL AROMATIC COMPOUNDS

(75) Inventors: Shyh-Yuan Hwang, Newton, MA (US); Maruti Bhandarkar, Joel Nagar (IN); Chung-Ming Chi, Weymouth, MA (US); Waheed Mukaddam, Cambridge, MA (US); Frank Demers, Holderness, NH (US); Richard F. Guarino, East Freetown, MA (US); Dana E Johnson, Hopkinton, MA (US)

(73) Assignee: Stone & Webster, Inc., Houston, TX (US)

( * ) Notice: Subject to any disclaimer, the term of this patent is extended or adjusted under 35 U.S.C. 154(b) by 1231 days.

(21) Appl. No.: 10/505,787

(22) PCT Filed: Feb. 27, 2003

(86) PCT No.: PCT/US03/05927

§ 371 (c)(1),
(2), (4) Date: Feb. 10, 2005

(87) PCT Pub. No.: WO03/074452

PCT Pub. Date: Sep. 12, 2003

(65) Prior Publication Data

US 2005/0143612 A1     Jun. 30, 2005

(51) Int. Cl.
C07C 2/66 (2006.01)
C07C 7/04 (2006.01)
(52) U.S. Cl. .................................. 585/448; 585/809
(58) Field of Classification Search .............. 585/448, 585/809
See application file for complete search history.

(56) References Cited

U.S. PATENT DOCUMENTS

| | | | |
|---|---|---|---|
| 3,326,998 A * | 6/1967 | Reusser et al. ............ 585/641 |
| 3,751,504 A | 8/1973 | Keown et al. |
| 4,016,218 A | 4/1977 | Haag et al. |
| 4,169,111 A | 9/1979 | Wight |
| 4,358,362 A | 11/1982 | Smith et al. |
| 4,459,426 A | 7/1984 | Inwood et al. |
| 4,547,605 A | 10/1985 | Kresge et al. |
| 4,849,569 A | 7/1989 | Smith, Jr. |
| 4,891,458 A | 1/1990 | Innes et al. |
| 4,950,834 A | 8/1990 | Arganbright et al. |
| 4,954,325 A | 9/1990 | Rubin et al. |
| 4,973,790 A | 11/1990 | Beech, Jr. et al. |
| 4,992,606 A | 2/1991 | Kushnerick et al. |
| 5,021,141 A | 6/1991 | Rubin |
| 5,030,786 A | 7/1991 | Shamshoum et al. |
| 5,053,579 A | 10/1991 | Beech, Jr. et al. |
| 5,077,445 A | 12/1991 | Le |
| 5,081,323 A | 1/1992 | Innes et al. |
| 5,086,193 A | 2/1992 | Sy |
| 5,157,185 A | 10/1992 | Chu et al. |
| 5,160,497 A | 11/1992 | Juguin et al. |
| 5,198,595 A | 3/1993 | Lee et al. |
| 5,236,575 A | 8/1993 | Bennett et al. |
| 5,240,889 A | 8/1993 | West et al. |
| 5,245,094 A | 9/1993 | Kocal |
| 5,250,277 A | 10/1993 | Kresge et al. |
| 5,258,565 A | 11/1993 | Kresge et al. |
| 5,292,698 A | 3/1994 | Chu et al. |
| 5,300,722 A | 4/1994 | Steigelmann et al. |
| 5,334,795 A | 8/1994 | Chu et al. |
| 5,362,697 A | 11/1994 | Fung et al. |
| 5,371,310 A | 12/1994 | Bennett et al. |
| 5,430,211 A | 7/1995 | Pogue et al. |
| 5,437,855 A | 8/1995 | Valyocsik |
| 5,453,554 A | 9/1995 | Cheng et al. |
| 5,493,065 A | 2/1996 | Cheng et al. |
| 5,522,984 A | 6/1996 | Gajda et al. |
| 5,536,894 A | 7/1996 | Degnan et al. |
| 5,557,024 A | 9/1996 | Cheng et al. |
| 5,563,311 A | 10/1996 | Chang et al. |

(Continued)

FOREIGN PATENT DOCUMENTS

EP      0432447      6/1991

(Continued)

OTHER PUBLICATIONS

Japanese Office Action issued Dec. 23, 2009 for corresponding Japanese Patent Application No. 2003/572926.

*Primary Examiner*—Thuan Dinh Dang
(74) *Attorney, Agent, or Firm*—Locke Lord Bissell & Liddell, LLP; Alan B. Clement; Peter J. Fallon

(57) ABSTRACT

Improved integrated processes for the production of alkyl aromatic compounds are disclosed wherein aromatic compounds which may be treated for removal of deleterious substances are reacted with olefin compounds, which may also be treated for contaminant removal, in the presence of acidic zeolite catalyst(s) to produce the desired alkyl aromatic compound(s). The aromatic and preferably also the olefin feeds are treated substantially to remove contaminants, particularly the nitrogen compounds contained therein, before they are brought together for reaction in the presence of the zeolite catalyst(s). In accordance with the present invention, it has been found that feed pretreatment for removal of nitrogen compounds significantly improves the run length and life of the acidic zeolite catalyst(s). The feed pretreatment of this invention may include the steps of distillation, extraction, and/or adsorption by solid adsorbent, which may be regenerated in accordance with further embodiments of this invention.

25 Claims, No Drawings

U.S. PATENT DOCUMENTS

| | | | |
|---|---|---|---|
| 5,569,805 | A | 10/1996 | Beck et al. |
| 5,672,799 | A | 9/1997 | Perego et al. |
| 5,689,025 | A | 11/1997 | Abichandani et al. |
| 5,744,686 | A | 4/1998 | Gajda |
| 5,900,520 | A | 5/1999 | Mazzone et al. |
| 5,902,917 | A | 5/1999 | Collins et al. |
| 5,904,073 | A | 5/1999 | Ghosh |
| 5,942,650 | A | 8/1999 | Gajda |
| 5,980,859 | A | 11/1999 | Gajda et al. |
| 6,049,018 | A | 4/2000 | Calabro et al. |
| 6,051,521 | A | 4/2000 | Chent et al. |
| 6,060,632 | A | 5/2000 | Takamatsu et al. |
| 6,096,935 | A | 8/2000 | Schulz et al. |
| 6,162,416 | A | 12/2000 | Gajda et al. |
| 6,232,515 | B1 | 5/2001 | Schulz et al. |
| 6,281,399 | B1 | 8/2001 | Schulz et al. |
| 6,297,417 | B1 | 10/2001 | Samson et al. |
| 6,313,362 | B1 | 11/2001 | Green et al. |
| 6,355,851 | B1 | 3/2002 | Wu et al. |
| 6,479,721 | B1 | 11/2002 | Gajda et al. |

FOREIGN PATENT DOCUMENTS

| | | |
|---|---|---|
| EP | 0 467 007 B1 | 4/1996 |
| JP | 03-210392 | 9/1991 |
| JP | 04198139 A | 7/1992 |
| JP | 2000-516248 | 12/2000 |
| WO | WO 98/07673 | 2/1998 |
| WO | WO 01/07383 A1 | 2/2001 |
| WO | WO 02/14240 A1 | 2/2002 |
| WO | WO 02/062734 A1 | 8/2002 |

* cited by examiner

PRODUCTION OF ALKYL AROMATIC COMPOUNDS

BACKGROUND OF THE INVENTION

Catalytic reaction of aromatics and olefins in the presence of acidic zeolite catalysts has been used in most of the advanced chemical processes for the production of alkyl aromatic compounds such as cumene and ethylbenzene. Since the early 1990s, new zeolite-based cumene technologies have been developed by Mobil/Badger, Dow/Kellogg, UOP, and others. These cumene technologies carry out the alkylation of benzene and propylene in liquid phase in the presence of a solid acidic zeolite catalyst. A process developed by CDTech effects alkylation of benzene and propylene in mixed phases in a catalytic distillation column which houses both distillation devices and bales of zeolite catalysts. Catalysts that can be used for alkylation of benzene with propylene and also for transalkylation of benzene and polyisopropylbenzenes in liquid phase include zeolite beta, zeolite Y, zeolite omega, ZSM-5, ZSM-12, MCM-22, MCM-36, MCM-49, MCM-56, MCM-58, MCM-68, Faujasite, Mordenite, porous crystalline magnesium silicates, and tungstate modified zirconia, all of which are known in the art.

MCM-22 and its use to catalyze the synthesis of alkyl aromatics are described, for example, in U.S. Pat. No. 4,954,325 (Rubin), U.S. Pat. No. 4,992,606 (Kushnerick), U.S. Pat. No. 5,077,445 (Le), U.S. Pat. No. 5,334,795 (Chu), and U.S. Pat. No. 5,900,520 (Mazzone), each of which is incorporated herein by reference. MCM-36 and its use in the synthesis of alkyl aromatics are described in U.S. Pat. No. 5,250,277 (Kresge), U.S. Pat. No. 5,292,698 (Chu), and U.S. Pat. No. 5,258,565 (Kresge), each of which is incorporated herein by reference. MCM-49 and its use in the synthesis of alkyl aromatics are described in U.S. Pat. No. 5,236,575 (Bennett), U.S. Pat. No. 5,493,065 (Cheng) and U.S. Pat. No. 5,371,310 (Bennett), each of which is incorporated herein by reference. MCM-56 and its use to catalyze the synthesis of alkyl aromatics are described in U.S. Pat. No. 5,362,697 (Fung), U.S. Pat. No. 5,453,554 (Cheng), U.S. Pat. No. 5,536,894 (Degnan), U.S. Pat. No. 5,557,024 (Cheng), and U.S. Pat. No. 6,051,521 (Cheng), each of which is incorporated herein by reference. MCM-58 and its use for the production of alkyl aromatics are described in U.S. Pat. No. 5,437,855 (Valyocsik) and U.S. Pat. No. 5,569,805 (Beck), each of which is incorporated herein by reference. MCM-68 and its use for the production of alkyl aromatics are described in U.S. Pat. No. 6,049,018 (Calabro), which is incorporated herein by reference.

The use of tungstate modified zirconia to catalyze the synthesis of alkyl aromatics is described in U.S. Pat. No. 5,563,311 (Chang), which is incorporated herein by reference. U.S. Pat. No. 5,081,323 (Innes), which is incorporated herein by reference, teaches a liquid phase alkylation or transalkylation process using zeolite beta. Production of cumene over zeolite Y is described in U.S. Pat. No. 5,160,497 (Juguin) and U.S. Pat. No. 5,240,889 (West), which are incorporated herein by reference. U.S. Pat. No. 5,030,786 (Shamshoum) and U.S. Pat. No. 5,980,859 (Gajda), and European patent 0,467,007 (Butler), which are incorporated herein by reference, describe the production of alkyl aromatic compounds with zeolite Beta, zeolite Y, and zeolite Omega. U.S. Pat. No. 5,522,984 (Gajda), U.S. Pat. No. 5,672,799 (Perego), U.S. Pat. No. 5,980,859 (Gajda), and U.S. Pat. No. 6,162,416 (Gajda), which are incorporated herein by reference, teach the production of cumene with zeolite beta. Use of zeolite Mordenite in production of monoalkylated benzene such as cumene and ethylbenzene is described in U.S. Pat. No. 5,198,595 (Lee), which is incorporated herein by reference. Production of ethylbenzene with ex situ selectivated zeolite catalyst is described in U.S. Pat. No. 5,689,025 (Abichandani), which is incorporated herein by reference.

The first zeolite-based ethylbenzene process, developed jointly by Mobil and Badger in the early 1980s, utilized vapor phase alkylation of benzene with ethylene and vapor phase transalkylation of benzene and polyethylbenzene. Both the alkylation and transalkylation steps of this early process were carried out in the presence of solid acidic ZSM-5 catalysts. Production of ethylbenzene with ZSM-5 is described in U.S. Pat. No. 5,157,185 (Chu), which is incorporated herein by reference.

Several liquid phase zeolite-based ethylbenzene technologies were developed in the late 1980s and in the 1990s by UOP/Lummus, Mobil/Badger, and others. Alkylation of benzene with ethylene and transalkylation of benzene and polyethylbenzenes were carried out in liquid phase in the presence of solid acidic zeolite catalysts. Catalysts that can be used for alkylation of benzene with ethylene and transalkylation of benzene and polyethylbenzenes in liquid phase processes include zeolite beta, zeolite Y, zeolite omega, ZSM-5, ZSM-12, MCM-22, MCM-36, MCM-49, MCM-56, MCM-58, MCM-68, Faujasite, Mordenite, porous crystalline magnesium silicates, and tungstate modified zirconia. A process developed by CDTech effects alkylation of benzene and ethylene in mixed phases in a catalytic distillation column which houses both distillation devices and bales of zeolite catalysts.

Production of ethylbenzene over intermediate pore size zeolites is described in U.S. Pat. No. 3,751,504 (Keown), U.S. Pat. No. 4,547,605 (Kresge), and U.S. Pat. No. 4,016,218 (Haag), which are incorporated herein by reference. U.S. Pat. No. 4,169,111 (Wight) and U.S. Pat. No. 4,459,426 (Inwood), which are incorporated herein by reference, disclose production of ethylbenzene over large pore size zeolites such as zeolite Y. Synthesis of zeolite ZSM-12 is described in U.S. Pat. No. 5,021,141 (Rubin), which is incorporated herein by reference. A process for ethylbenzene production over zeolite ZSM-12 is described in U.S. Pat. No. 5,907,073 (Kumar), which is incorporated herein by reference. Production of ethylbenzene over zeolite Mordenite is described in U.S. Pat. No. 5,430,211 (Pogue), which is incorporated herein by reference. Liquid phase synthesis of ethylbenzene with zeolite Beta is described in U.S. Pat. No. 4,891,458 (Innes) and U.S. Pat. No. 6,060,632 (Takamatsu), which are incorporated herein by reference. U.S. Pat. No. 4,849,569 (Smith), U.S. Pat. No. 4,950,834 (Arganbright), U.S. Pat. No. 5,086,193 (Sy), U.S. Pat. No. 5,113,031 (Sy), and U.S. Pat. No. 5,215,725 (Sy), which are incorporated herein by reference, teach various systems for the catalytic distillation production of alkylated aromatic compounds, including ethylbenzene and cumene.

U.S. Pat. No. 5,902,917 (Collins), which is incorporated herein by reference, teaches a process for producing alkylaromatics, especially ethylbenzene and cumene, wherein a feedstock is first fed to a transalkylation zone and the entire effluent from the transalkylation zone is then cascaded directly into an alkylation zone along with an olefin alkylating agent, especially ethylene or propylene.

U.S. Pat. No. 6,096,935 (Schulz), which is incorporated herein by reference, teaches a process for producing alkyl aromatics using a transalkylation reaction zone and an alkylation reaction zone. The transalkylation reaction zone effluent passes to the alkylation reaction zone where aromatics in the transalkylation reaction zone effluent are alkylated to the desired alkyl aromatics. U.S. Pat. Nos. 6,232,515 and 6,281, 399 (Schulz), which are incorporated herein by reference, teach further details of processes for producing ethyl and isopropyl aromatics using a transalkylation reaction zone and an alkylation reaction zone.

U.S. Pat. No. 6,479,721 (Gadja), which is incorporated herein by reference, teaches a process for the alkylation of aromatics with olefins using a solid catalyst wherein the olefin ratio and/or the maximum olefin concentration in the alkylation catalyst bed is maintained less than an upper limit to reduce the catalyst deactivation rate and the formation of diphenylalkanes.

PCT published application WO02062734 (Chen), which is incorporated herein by reference, teaches a process for producing a monoalkylation aromatic product, such as ethylbenzene and cumene, utilizing an alkylation zone and a transalkylation zone in series or a combined alkylation and transalkylation reactor zone. This invention claims to minimize the amount of excess aromatic material that is used and needs to be recovered and subsequently circulated, thus minimizing the production cost.

U.S. Pat. No. 6,313,362 (Green), which is incorporated herein by reference, teaches an aromatic alkylation process in which the alkylation product is contacted with a purification medium in a liquid phase pre-reaction step to remove impurities and to form a purified stream. The purified stream may then be further processed by liquid phase transalkylation to convert the polyalkylated aromatic compound to a monoalkylated aromatic compound. The process may use a large pore molecular sieve catalyst such as MCM-22 as the purification medium in the pre-reaction step because of its high reactivity for alkylation, strong retention of catalyst poisons, and low reactivity for oligomerization under the pre-reactor conditions. Olefins, diolefins, styrene, oxygenated organic compounds, sulfur-containing compounds, nitrogen-containing compounds and oligomeric compounds are claimed to be removed by this process.

U.S. Pat. No. 4,358,362 (Smith), which is incorporated herein by reference, teaches a method for enhancing catalytic activity of a zeolite catalyst by contacting a feed stream which contains a catalytically deleterious impurity with a zeolitic sorbent. This invention is applicable to a variety of processes including dewaxing, with an example illustrating a temperature reduction of 100° F. of the initial equilibrium (lineout) temperature by the method of the invention.

Japanese patents JP4198139 and 717536 (Hidekichi), which are incorporated herein by reference, teach a production process for alkylbenzene including a step of pretreatment of benzene for reduction of base compounds prior to the alkylation of benzene over acid catalysts. The removal of basic material in benzene is achieved by contacting the benzene feed stream with clay, zeolite, activated coal, silica gel, alumina, and ion exchange resin.

U.S. Pat. No. 4,973,790 (Beech), which is incorporated herein by reference, teaches a process for oligomerizing $C_2$ to $C_{10}$ olefins obtained by catalytic cracking of heavy crude oil. The olefins are oligomerized in the presence of added hydrogen over a shape-selective zeolite to gasoline and distillate products. Feed pretreatment to remove basic nitrogen compounds present in the light olefin refinery stream uses a water wash or a guard bed to improve catalyst life.

A process for upgrading of unstable olefins, naphthas, and dienes, such as coker naphthas, is taught in U.S. Pat. No. 5,053,579 (Beech), which is incorporated herein by reference. The olefins are oligomerized over a zeolite catalyst to gasoline and distillate products. Addition of hydrogen and feed pretreatment to remove basic nitrogen compounds are taught to improve catalyst life. Water washing of coker naphtha is the preferred method of removing basic nitrogen compounds.

A process of producing linear alkyl benzene (LAB) is taught in U.S. Pat. No. 5,245,094 (Kocal), which is incorporated herein by reference. The catalyst life and the product linearity are improved by treating the olefinic feedstock obtained from dehydrogenation of paraffins to reduce the aromatics content thereof.

The positive or negative effects of moisture in zeolite catalyst and in the feed are discussed in several publications. For example, U.S. Pat. No. 5,030,094 (Shamshoum), which is incorporated herein by reference, teaches a process for production of ethylbenzene in which the catalyst lifetime is increased by reducing the concentration of water in the feed to the reactor. By contrast, U.S. Pat. No. 5,240,889 (West), which is incorporated herein by reference, teaches a catalyst composition for catalyzing the alkylation and transalkylation reactions in the production of ethylbenzene and cumene. This patent, however, teaches that increasing the water content in the catalyst increases the catalyst life.

U.S. Pat. No. 5,300,722 (Amundsen), which is incorporated herein by reference, teaches an oxygen-free aromatic alkylation process. In this process, an aromatic hydrocarbon is contacted with an alkylating agent in a reactor vessel in the absence of oxygen and in the presence of a silica-containing molecular sieve catalyst under liquid phase alkylation conditions. The absence of oxygen is said to significantly improve the catalyst life.

U.S. Pat. No. 5,744,686 (Gajda), which is incorporated herein by reference, teaches a process for the removal of nitrogen compounds from an aromatic hydrocarbon stream by contacting the stream with a selective adsorbent having an average pore size less than about 5.5 Angstroms. The selective adsorbent is a non-acidic molecular sieve selected from the group consisting of pore closed zeolite 4A, zeolite 4A, zeolite 5A, silicalite, F-silicalite, ZSM-5, and mixture thereof. One embodiment taught in this patent includes a combination of a fractionation zone and an adsorption zone.

U.S. Pat. No. 5,942,650 (Gajda), which is incorporated herein by reference, is an extension of U.S. Pat. No. 5,744,686 and applies the invention to aromatic alkylation with ethylene and propylene, isomerization, and disproportionation. The pore size of the catalyst used for those reactions is at least 6 Angstroms.

A process for preparing an alkylated benzene or mixture of alkylated benzenes is taught in U.S. Pat. No. 6,297,417 (Samson), which is incorporated herein by reference. The process includes contacting a benzene feedstock with a solid acid, such as acidic clay or acidic zeolite, in a pretreatment zone at a temperature between about 130° C. and about 300° C. It is taught that such a pretreatment step improves the lifetime of the alkylation and transalkylation catalyst.

U.S. Pat. No. 6,355,851 (Wu), which is incorporated herein by reference, teaches a zeolite-catalyzed cumene synthesis process in which benzene and propylene feedstocks are pretreated to remove catalyst poisons. The benzene feedstock is pretreated under pressure by contact with a "hot" clay bed at a temperature of about 200 to 500° C., followed by distillation of the benzene feedstock to separate the benzene from the higher molecular weight materials formed from olefinic poisons during the hot clay treatment The benzene feed is also subjected to a "cold" clay treatment wherein the benzene distillate is contacted with an ambient-temperature clay. The propylene feedstock is pretreated by contact with an alumina to remove trace sodium compounds and moisture, a molecular sieve to remove water, and two modified aluminas to remove catalyst poisons. The pretreated propylene and benzene feedstocks are then reacted in the presence of a zeolite catalyst to form cumene without causing rapid degradation of the catalyst's activity.

A method for purifying olefin-containing feed streams in polymerization or alkylation processes, which is characterized by the fact that the feed stream is passed over an adsorption layer is taught in PCT published application WO0107383, which is incorporated herein by reference.

PCT published application WO0214240 (Venkat), which is incorporated herein by reference, teaches removal of polar contaminants in an aromatic feedstock by contacting it with molecular sieves with pore size greater than 5.6 Angstroms at temperatures below 130° C.

These prior art processes, however, fail to teach a complete and consistently effective approach to eliminating deleterious substances from hydrocarbon feedstocks used for alkylation and/or transalkylation processes to prevent poisoning of the acidic zeolite catalysts preferred for such processes. The limitations and deficiencies of these prior art techniques are overcome in whole or at least in part by the improved integrated processes of this invention.

OBJECTS OF THE INVENTION

Accordingly, a principal object of this invention is to provide improved methods and processes and related apparatus for the pretreatment of hydrocarbon feedstocks prior to contact with alkylation and/or transalkylation acidic zeolite catalyst bed(s) to remove or substantially reduce impurities in such feedstocks which otherwise might adversely affect the performance, operation or life of the catalyst bed(s).

A general object of this invention is to provide pretreated hydrocarbon feedstocks which are substantially free of impurities which could damage downstream catalyst bed(s) used for alkylation, transalkylation and similar processes.

Another general object of this invention is to provide one or a combination of pretreatment steps for purifying one or more hydrocarbon feed streams prior to a downstream catalytic process step.

A specific object of this invention is to provide methods and apparatus for treating an olefin or aromatic feedstock for removal of organic or inorganic nitrogen compounds in preparation for a catalytic alkylation or transalkylation process.

Another specific object of this invention is to provide a hydrocarbon feedstock pretreatment method comprising one or a combination of distillation, extraction, and/or adsorption steps for removing or substantially reducing impurities which might poison a downstream catalyst bed.

Yet another specific object of this invention is to provide an in-line guard bed packed with a suitable adsorbent for pretreating a hydrocarbon feed stream to remove or substantially reduce nitrogen compounds before contacting the feed stream with catalyst bed(s).

Other objects and advantages of the present invention will in part be obvious and will in part appear hereinafter. The invention accordingly comprises, but is not limited to, the methods, processes and related apparatus, involving the several steps and the various components, and the relation and order of one or more such steps and components with respect to each of the others, as exemplified by the following description. Various modifications of and variations on the methods and apparatus as herein described will be apparent to those skilled in the art, and all such modifications and variations are considered within the scope of the invention.

SUMMARY OF THE INVENTION

Although production of alkyl aromatic compounds like cumene and ethylbenzene in the presence of acidic zeolite catalysts has attained much commercial success, the susceptibility of acidic zeolite catalysts to deactivation has severely limited catalyst run length and catalyst life. In accordance with the present invention, it has now been found that nitrogen-containing impurities in one or both feedstocks may neutralize the acidic active sites on the acidic zeolite catalyst and thereby reduce catalyst activity and its ability to effect the desired reaction. Long-term accumulation of these nitrogen-containing impurities on the catalyst gradually reduces catalyst activity to the point where plant performance becomes unacceptable, requiring that the plant be shutdown to reactivate, regenerate, or replace the catalyst.

The cost of such a plant shutdown often includes not only the cost of the operations required to bring plant performance back to a desirable or commercially acceptable level but also includes the lost profit the producer failed to realize from sale of the product which otherwise could have been produced during the plant shutdown. In some cases, frequent reactivation or regeneration of the poisoned catalyst also reduces catalyst life. In such cases, additional catalyst replacement cost is also incurred.

Pretreatment of one or both feedstocks to remove nitrogen compounds and/or other contaminants which are present in amounts sufficient to adversely affect the performance of an acidic zeolite catalyst by one or a combination of pretreatment processes in accordance with this invention prior to alkylation and/or transalkylation, together with regeneration of adsorbents used in an adsorption pretreatment, has now been found to be the most cost-effective way to minimize the costs association with harmful impurities in the feedstock(s).

DETAILED DESCRIPTION OF PREFERRED EMBODIMENTS

A. Distillation Pretreatment Processes

Some impurities that may adversely affect the performance of acidic zeolite catalyst(s) have very high or very low volatility relative to the feedstock, and these can typically best be readily removed by distillation processes. Two such examples are solvents used in benzene extraction: n-formyl morpholine (NFM) and n-methylpyrrolidinone (NMP). Both NFM and NMP have been found to be poisons to acidic zeolite catalysts. These solvents also have very high boiling points relative to benzene, and thus can be efficiently and economically separated from benzene by distillation. As another example, ammonia has a very high volatility relative to propylene and thus can be effectively and economically separated from propylene by distillation.

In some cases both impurities (e.g., nitrogen compounds) lighter (more volatile) than the feedstock and those heavier (less volatile) than the feedstock may be removed by distillation in a single distillation column or, alternatively, in a series of columns. In the case of a single column operation, light impurities are removed at or near the top of the column, heavy impurities are removed at or near the bottom of the column, and the pretreated feedstock is recovered as a side draw from a middle portion of the column.

Some impurities, including nitrogen compounds, may also be removed from a feedstock by distillation in the same distillation apparatus where other light and/or heavy impurities are also removed at the same time. In some cases, the heavy nitrogen compounds and/or other heavy impurities are removed at or near the bottom of the column while the pretreated and purified feedstock is recovered at or near the top of the column. In some other cases, the light nitrogen compounds and/or other light impurities are removed at or near the top of the column and the pretreated and purified feedstock is recovered at or near the bottom of the column. In yet some other cases, light nitrogen compounds and/or other light impurities are removed at or near the top of the column, heavy nitrogen compounds and/or other heavy impurities are removed at or near the bottom of the column, and the pretreated and purified feedstock is recovered as a side draw from a middle portion of the column.

B. Extraction Pretreatment Processes

Some feedstock impurities can best be removed from a feedstock by extraction processes wherein a suitable extractant is used to separate a contaminant that is preferentially soluble in the extractant from the feedstock. Ammonia, for example, a known poison to many zeolite catalysts, has very high solubility in water relative to propylene and thus typically can be easily removed from propylene by a water wash wherein the water may or may not be acidified.

C. Selective Adsorption Pretreatment Processes

Some feedstock impurities can best be removed from a feedstock by selective adsorption processes using suitable preferably regenerable adsorbents. Suitable regenerable adsorbents for purposes of this invention which can be effectively regenerated multiple times in situ have been found to include acidic clay, zeolite catalysts, molecular sieves, activated alumina, activated carbon, silica gel, and ion exchange resins. Over a period of use, which will vary according to the nature of the adsorbent, the nature of the feedstock being treated and the impurities contained therein, the concentration of impurities in the feedstock, and temperature and pressure conditions, the adsorbent will gradually lose at least a portion of its activity and effectiveness. At some point, the activity or effectiveness of the adsorbent will be reduced to a point where continued use is no longer considered viable practically or commercially or both. Such a used adsorbent is defined herein as "spent adsorbent," which can be discarded and replaced or, alternatively, in accordance with this invention, can be regenerated. It has been found that certain spent adsorbents can usually be effectively regenerated multiple times in situ by removing the adsorbed contaminants under favorable conditions. It has now been found that effective regeneration of certain adsorbents can be accomplished by subjecting the adsorbents, under elevated temperatures, to a flow of a substantially inert gas (i.e., inert relative to the adsorbent) such as nitrogen, air, natural gas, liquefied petroleum gas, methane, ethane, propane, butanes, pentanes, or steam, or to a flow of a substantially inert liquid such as liquefied petroleum gas, ethane, propane, butanes, pentanes, hexanes, benzene, toluene, or xylenes. It has further been found that some adsorbents can also be regenerated by displacing the adsorbed contaminants by other compound(s) which is (are) preferentially adsorbed on the adsorbent more strongly than the originally-adsorbed contaminant(s). Because water is typically very strongly adsorbed on most of the aforementioned adsorbents, water or mixtures containing a high level of water can typically be used to effectively preferentially displace adsorbed contaminants from the adsorbents. Some adsorbents may also be regenerated by acid treatments such as by washing with a stream of acidic mixtures.

D. Embodiments of the Present Invention

A first embodiment of the present invention is to pretreat only the olefin feed to an alkylation and/or transalkylation process if the aromatic feed to the process is considered substantially free of impurities which may be harmful to the zeolite catalyst(s) employed in one or more catalyst beds in a section of the process. The olefin feed can be pretreated in accordance with the present invention as it enters the process, or together with other pretreatment and/or purification steps, or alternatively after other pretreatment and/or upstream purification steps have been completed but prior to contacting the catalyst bed(s). The aforementioned other pretreatment and/or upstream purification steps, where applicable, are used to reduce other impurities in a feed which may adversely affect the performance of the zeolite catalyst(s), the purity of the desired alkyl aromatic product, or other performance or product quality characteristics of the process.

Another embodiment of the present invention is to pretreat only the aromatic feed to an alkylation and/or transalkylation process if the olefin feed to the process is deemed substantially free of impurities which may be harmful to the zeolite catalyst(s) used in one or more catalyst beds in a reaction section of the process. The aromatic feed can be pretreated in accordance with the present invention as it enters the process, or together with other pretreatment and/or purification steps, or alternatively after other pretreatment and/or upstream purification steps have been completed but prior to contacting the catalyst bed(s). The aforementioned other pretreatment and/or upstream purification steps, where applicable, are used to reduce other impurities in a feed which may adversely affect the performance of the zeolite catalyst, the purity of the desired alkyl aromatic product, or other performance or product quality characteristics of the process.

The aromatic feed stream may also be pretreated in accordance with this invention together with other streams in the process or after it has been pretreated and/or purified together with other streams in the process by other pretreatment and/or purification steps. The aforementioned other pretreatment and/or purification steps, where applicable, are used to reduce other impurities in the feed which may adversely affect the performance of the zeolite catalyst(s), the purity of the desired alkyl aromatic product, or other performance or product quality characteristics of the process.

Yet another embodiment of this invention is to pretreat both the olefin and the aromatic feeds to an alkylation and/or transalkylation process if both the olefin feed and the aromatic feed are known to contain or are suspected of containing material which may be harmful to the zeolite catalyst(s) employed in one or more catalyst beds in a reaction section of the process. In this embodiment of the invention, the olefin feed can be pretreated in accordance with the present invention as it enters the process, or together with other pretreatment and/or purification steps, or alternatively after other pretreatment or upstream purification steps have been completed but prior to contacting the catalyst bed(s). The aforementioned other pretreatment and/or upstream purification steps, where applicable, are used to reduce other impurities in the feeds which may adversely affect the performance of the zeolite catalyst(s), the purity of the desired alkyl aromatic product, or other performance or product quality characteristics of the process. Also, in this embodiment of the invention, the aromatic feed stream can be pretreated in accordance with the present invention as it enters the process, or together with other pretreatment and/or purification steps, or alternatively after other pretreatment and/or upstream purification steps have been completed but prior to contacting the catalyst bed (s). The aforementioned other pretreatment and/or upstream purification steps, where applicable, are used to reduce other impurities in the feeds which may adversely affect the performance of the zeolite catalyst(s), the purity of the desired alkyl aromatic product, or other performance or product quality characteristics of the process.

The aromatic feed stream may also be pretreated in accordance with this embodiment of the invention together with other streams in the process, or after it has been pretreated and/or purified together with other streams in the process by other pretreatment and/or purification steps. The aforementioned other pretreatment and/or purification steps, where applicable, are used to reduce other impurities in the feed which may adversely affect the performance of the zeolite catalyst(s), the purity of the desired alkyl aromatic product, or other performance or product quality characteristics of the process.

In appropriate circumstances, any two or even all three of the distillation, extraction and selective adsorption feed pretreatment processes of this invention can be integrated with one another and with an adsorbent regeneration step as taught herein and utilized in any convenient order or sequence to obtain a high-efficiency, highly effective, custom-tailored integrated process adaptable to meet the needs of handling different feeds containing different possible contaminants over a wide range of operating parameters.

Although some of the prior art processes suggest removal of at least some nitrogen compounds by contacting a feed to be purified with a selective adsorbent, they fail to address the advantages of using regenerable adsorbent(s), or to teach various methods suitable and effective for multiple in-situ regeneration of spent adsorbents, or to demonstrate the effectiveness of multiple in-situ regeneration methods according to this invention in successfully restoring the adsorption effectiveness and successfully recovering at least a certain minimum acceptable adsorption capacity of the spent adsorbent, or to stress the importance of reliable multiple adsorbent regeneration for process efficiency. As essentially all selective adsorbents cited in prior art processes have limited adsorption capacity, it is crucial that an adsorbent used in a pretreatment process be capable of being regenerated multiple times in-situ substantially to restore its original adsorption effectiveness and to recover at least a certain minimum acceptable adsorption capacity so that it can be re-used multiple times successfully. We have found that the regenerability of the adsorbents often becomes the crucial factor in determining if a selective adsorption feed pretreatment process is economically viable. If spent adsorbent cannot be regenerated multiple times substantially to restore its original adsorption effectiveness and recover at least a certain minimum acceptable adsorption capacity so that it can be re-used in its original adsorption service, it will need to be removed from the treatment vessel once is has become spent and replaced with a fresh load of adsorbent The material cost of periodically providing a new load of adsorbent together with the labor cost required to purchase, transport, store, and load the fresh adsorbent into the treatment vessel(s) as well as to unload, store, transport, and dispose of the spent adsorbent add up very quickly and render pretreatment processes of the prior art generally economically unattractive.

In addition, the prior art fails to teach that there are various alternative pretreatment processes appropriate for removal of different contaminants from different feeds or that such processes can often be combined and integrated with and/or carried out together with other pretreatment and/or purification steps used to reduce other impurities which may adversely affect the performance of the alkylation/transalkylation catalyst(s), the purity of the desired alkyl aromatic product, or other performance or product quality characteristics of the overall alkyl aromatic production process. By carrying out together with, and/or in combination with, other pretreatment and/or purification steps, the capital and operating costs for removal of nitrogen compounds and/or other contaminants can be significantly reduced and/or minimized. For example, ammonia contaminants in a propylene feedstock may be easily removed from the feed by adding a few trays in a distillation column to be built for purification of the said propylene feedstock. In this case, the cost of removal of ammonia from propylene is minimized as the cost of additional trays is minimal and essentially no additional operating costs are incurred.

The following examples provide illustrative embodiments of the present invention.

EXAMPLE 1

A propylene feed containing 20 ppm by weight of ammonia was pretreated in accordance with an embodiment of this invention by being fed at the rate of 72 grams per hour to a guard bed containing 20.3 grams of Selexsorb CD supplied by Alcoa. The guard bed was maintained at 30° C. A sample of the treated propylene taken after 78 grams of propylene had passed through the guard bed was found to contain only 0.03 ppm by weight of ammonia, thereby demonstrating the effectiveness of the guard bed in reducing the ammonia content of the propylene feed.

EXAMPLE 2

The same guard bed and the same propylene feed containing 20 ppm by weight of ammonia as used in Example 1 above were used in this example. The propylene flowrate was now slightly decreased to 71 grams per hour, and the guard bed temperature was raised to 57° C. in this example. After another 77 grams of propylene had been treated, an effluent sample was taken. The ammonia content in the effluent sample was found to be only 0.01 ppm by weight of ammonia, thereby demonstrating the continuing effectiveness of the guard bed in removing ammonia from the feed.

EXAMPLE 3

A propylene feed containing about 110 ppm by weight of moisture (water) and 1.3 ppm by weight of ammonia was pretreated in accordance with another embodiment of the invention by being fed at a flow rate of about 90 grams per hour to two guard beds arranged in series, each prepared in accordance with the present invention. The first guard bed contained 60 grams of molecular sieve 3A supplied by PQ Corp. and was intended to remove moisture from the propylene stream. The second guard bed contained 10 grams of Molecular Sieve 13X supplied by Grace Davison and was intended to remove ammonia from the propylene stream. Both guard beds were maintained at 35° C.

Effluent samples from the second guard bed were taken on a regular basis to determine the ammonia content in the pretreated propylene stream. The ammonia content in the pretreated propylene stream remained below the lower detection limit of 0.01 ppm by weight even after more than 99 kilograms of propylene had been treated.

EXAMPLE 4

A benzene feed containing 15 ppm by weight of moisture and 7 ppm by weight of NFM was pretreated in accordance with another embodiment of the invention by being fed to a guard bed prepared in accordance with the present invention containing 10 grams of Molecular Sieve 13X supplied by Aldrich Chemical Co. The benzene flowrate was 110 grams per hour, and the guard bed was maintained at an ambient temperature of about 25° C.

Effluent samples from the guard bed were taken regularly to determine the NFM content in the pretreated stream. The NFM content in the pretreated benzene stream was less than 0.03 ppm by weight after 10 kilograms of benzene had been treated.

EXAMPLE 5

A benzene feed containing about 15 ppm by weight of moisture and 7 ppm by weight of NMP was pretreated in accordance with another embodiment of the invention by being fed at a flowrate of 110 grams per hour to a guard bed prepared in accordance with the present invention containing 10 grams of Molecular Sieve 13X. The guard bed was maintained at an ambient temperature of about 25° C.

Effluent samples from the guard bed were taken regularly to determine the NMP content in the pretreated stream. The NMP content in the pretreated benzene stream was less than 0.01 ppm by weight after 10 kilograms of benzene had been treated.

EXAMPLE 6

A benzene feed containing about 25 ppm by weight of moisture and 35 ppm by weight of NFM was pretreated in accordance with another embodiment of the invention by being fed at a flowrate of 110 grams per hour to a guard bed prepared in accordance with the present invention containing 10 grams of Molecular Sieve 13X supplied by PQ Corp. The guard bed was maintained at about 110° C.

Effluent samples from the guard bed were taken regularly to determine the NFM content in the pretreated stream. The NFM content in the pretreated benzene stream was less than 0.01 ppm by weight after 5 kilograms of benzene had been treated. This unit was thereafter operated continuously until NFM broke through and its content in the pretreated benzene stream was found to exceed 0.05 ppm by weight. The unit was then shutdown and the spent adsorbent was regenerated in situ at 235° C. under a continuous nitrogen purge for about 24 hours.

At this point, the regenerated adsorbent was cooled down and the nitrogen purge was terminated. The adsorbent was returned to its adsorption service at 110° C. with 110 grams per hour of benzene feed containing 20-25 ppm by weight of moisture and 35 ppm by weight of NFM. Regular analysis of the effluent sample confirmed the NFM content in the pretreated benzene stream being maintained below 0.01 ppm by weight after 5 kilograms of benzene had been treated. This unit was thereafter again operated continuously until NFM broke through and its content in the pretreated benzene stream was found to exceed 0.05 ppm by weight. The unit was then shutdown and the spent adsorbent again regenerated in situ at 235° C. under a continuous nitrogen purge for about 24 hours before it was cooled down and the nitrogen purge terminated. The adsorbent was again returned to its adsorption service at 110° C. with 110 grams per hour of benzene feed containing 20-25 ppm by weight of moisture and 35 ppm by weight of NFM. Regular analysis of the effluent sample again confirmed the NFM content in the pretreated benzene stream being maintained below 0.01 ppm by weight after 5 kilograms of benzene had been treated.

In summary, the regenerable adsorbent used in this example was regenerated in-situ two times with nitrogen at elevated temperature in accordance with this invention. The adsorption effectiveness of the regenerated adsorbent was found to be fully restored after each regeneration such that the effluent sample was found to contain less than 0.01 ppm by weight of NFM. In addition, the regenerated adsorbent was found to be capable of pretreating at least 5 kilograms of benzene feed containing 20-25 ppm by weight of moisture and 35 ppm by weight of NFM. This example thus demonstrates the effectiveness of multiple regenerations using nitrogen at elevated temperature in restoring the adsorption effectiveness and recovering at least a minimum acceptable adsorption capacity of the spent adsorbent used in removing NFM and other nitrogen contaminants from a feed.

EXAMPLE 7

A benzene feed containing about 50 ppm by weight of moisture and 35 ppm by weight of NFM was pretreated in accordance with another embodiment of the invention by being fed at a flowrate of 110 grams per hour to a guard bed prepared in accordance with the present invention containing 10 grams of Molecular Sieve 13X. The guard bed was maintained at about 110° C.

Effluent samples from the guard bed were taken regularly to determine the NFM content in the pretreated stream. The NFM content in the pretreated benzene stream was less than 0.01 ppm by weight after 5 kilograms of benzene had been treated. This unit was thereafter operated continuously until NFM broke through and its content in the pretreated benzene stream was found to exceed 0.05 ppm by weight. The unit was then shutdown and the spent adsorbent was regenerated in situ at 200° C. under a continuous steam purge for about 16 hours. The regenerated adsorbent was then dried in nitrogen purge for about 4 hours.

After the regenerated adsorbent was cooled down and the nitrogen purge terminated, it was returned to its adsorption service at 110° C. with 110 grams per hour of benzene feed containing 50 ppm by weight of moisture and 35 ppm by weight of NFM. Regular analysis of the effluent sample confirmed the NFM content in the pretreated benzene stream being maintained below 0.01 ppm by weight after 5 kilograms of benzene had been treated. The unit was thereafter again operated continuously until NFM broke through and its content in the pretreated benzene stream was found to exceed 0.05 ppm by weight. The unit was then shutdown and the spent adsorbent regenerated again in situ at 200° C. under a continuous steam purge then dried in nitrogen purge.

After the regenerated adsorbent was cooled down and the nitrogen purge terminated, it was again returned to its adsorption service at 110° C. with 110 grams per hour of benzene feed containing 50 ppm by weight of moisture and 35 ppm by weight of NFM. Regular analysis of the effluent sample again confirmed the NFM content in the pretreated benzene stream being maintained below 0.01 ppm by weight after 5 kilograms of benzene had been treated.

The unit was thereafter again operated continuously until NFM broke through and its content in the pretreated benzene stream was found to exceed 0.05 ppm by weight. The adsorbent was then regenerated with steam, dried with nitrogen, and cooled down in nitrogen the third time at essentially identical conditions as before and returned to its adsorption service. The regenerated adsorbent was again confirmed to be capable of pretreating more than 5 kilograms of benzene containing 50 ppm by weight moisture and 35 ppm by weight NFM while the effluent NFM level remained below 0.01 ppm by weight.

In summary, the regenerable adsorbent used in this example was regenerated in-situ three times with steam at elevated temperature in accordance with this invention. The adsorption effectiveness of the regenerated adsorbent was found to be fully restored after each regeneration such that the effluent sample was found to contain less than 0.01 ppm by weight of NFM. In addition, the regenerated adsorbent was found to be capable of pretreating at least 5 kilograms of benzene feed containing about 50 ppm by weight of moisture and 35 ppm by weight of NFM. This example thus demonstrates the effectiveness of multiple regenerations using steam at elevated temperature in restoring the adsorption effectiveness and recovering at least a minimum acceptable adsorption capacity of the spent adsorbent used in removing NFM and other nitrogen contaminants from a feed.

EXAMPLE 8

A batch of MCM-22 type catalyst was loaded into a pilot plant alkylation reactor and tested for cumene synthesis. Between the catalyst on-stream hours of 5,603 and 5,630, the benzene charge was about 65 grams per hour, and the propylene charge was about 29 grams per hour. The reactor temperature was 128° C., and the propylene conversion was stable at greater than 99.99%.

At 5,631 on-stream hours, the pure benzene feed was replaced with a prepared benzene feed spiked with 50 ppm NMP. At the same time, a guard bed in accordance with the present invention containing 22.5 grams of molecular sieve 13X was placed into service upstream of the pilot plant alkylation reactor to pretreat the benzene feed for removal of the NMP. The guard bed was maintained at an ambient temperature of about 25° C. No NMP was detected in the benzene feed at the outlet of the guard bed, and the catalyst in the alkylation reactor remained stable during this period. The propylene conversion remained above 99.99%. This example demonstrated the effectiveness of a guard bed prepared and operated in accordance with this invention in removing NMP from the benzene feed thereby preventing catalyst deactivation.

At 5,652 on-stream hours, the molecular sieve 13X guard bed was by-passed and the NMP-containing benzene feed was fed to the reactor without pretreatment in accordance with this invention. Changes were soon apparent in the reactor temperature profile suggesting catalyst poisoning was occurring. Later, the NMP-containing benzene feed was replaced with a pure benzene feed. At 5,676 hours on-stream, the propylene conversion was found to have dropped to below 99.98%, thereby suggesting damage to or deterioration of the catalyst bed resulting from catalyst poisoning by the NMP.

It will be apparent to those skilled in the art that other changes and modifications may be made in the above-described apparatus and methods for pretreating one or more hydrocarbon feeds to an alkylation and/or transalkylation reactor for removal of substances harmful to the alkylation and/or transalkylation catalyst without departing from the scope of the invention herein, and it is intended that all matter contained in the above description shall be interpreted in an illustrative and not a limiting sense.

Having described the invention what is claimed is:

1. In a process for producing desired alkyl aromatic compound(s) by reacting an olefin feed with an aromatic feed in a reaction section in the presence of acidic zeolite catalyst(s) wherein the olefin feed contains at least a contaminant in an amount sufficient to adversely affect the performance of the acidic zeolite catalyst(s), the improvements comprising:
    (a) treating the olefin feed to said reaction section by distillation to substantially separate nitrogen contaminants having high volatility relative to said olefin feed, or nitrogen contaminants having low volatility relative to said olefin feed, or both from the olefin feed, such contaminants are present in the olefin feed in amounts sufficient to adversely affect the performance of the acidic zeolite catalyst(s), wherein said nitrogen contaminant(s) comprises at least one of n-formyl morpholine, n-methylpyrrolidinone and ammonia; and,
    (b) passing the olefin feed pretreated in accordance with step (a) to said reaction section.

2. A process according to claim 1, wherein the olefin feed is pretreated as it enters the process, together with pretreatment and/or purification steps other than distillation, or after pretreatment and/or purification steps other than distillation, but prior to entering the reaction section.

3. A process according to claim 2, wherein said olefin feed pretreatment includes at least one distillation step and said pretreatment and/or purification steps other than distillation are extraction with a suitable extractant to substantially separate nitrogen contaminants and/or selective adsorption with a regenerable adsorbent to substantially separate nitrogen contaminants.

4. A process according to claim 1, wherein said olefin feed pretreatment includes at least one distillation step in which at least a nitrogen contaminant is removed at or near the top of a distillation column and the pretreated olefin feed is recovered at or near the bottom of the column.

5. A process according to claim 1, wherein said olefin feed pretreatment includes at least a distillation step in which at least a nitrogen contaminant is removed at or near the bottom of a distillation column and the pretreated olefin feed is recovered at or near the top of the column.

6. A process according to claim 1, wherein said olefin feed pretreatment includes at least one distillation step in which at least a nitrogen compound that is lighter relative to the olefin feed and/or other impurities that are lighter relative to the olefin feed are removed at or near the top of a distillation column and at least a nitrogen compound that is heavier relative to the olefin feed and/or other impurities that are heavier relative to olefin feed are removed at or near the bottom of the distillation column, and the pretreated olefin feed is recovered as a side draw.

7. A process according to claim 1, wherein said olefin feed contains olefins containing 2 to 4 carbon atoms.

8. A process according to claim 1, wherein said olefin feed contains at least one member selected from the group consisting of ethylene, propylene, 1-butene, cis-2-butene, trans-2-butene, isobutene, and mixtures thereof.

9. A process according to claim 1, wherein said desired alkyl aromatic compound(s) consists of at least one member selected from the group consisting of ethylbenzene, cumene, n-propyl benzene, butylbenzenes, diethylbenzenes, diisopropylbenzenes, dibutylbenzenes, ethyltoluenes, cymenes, butyltoluenes, ethylcumenes, butyl ethylbenzenes, butylcumenes, and mixtures thereof.

10. A process according to claim 1, wherein said desired alkyl aromatic compound(s) consists of at least one member selected from the group consisting of: ethylbenzene, cumene, diethylbenzene isomer mixture, para-diethylbenzene, meta-diethylbenzene, diisopropylbenzene isomer mixture, para-diisopropylbenzene, meta-diisopropylbenzene, and mixtures thereof.

11. A process according to claim 1, wherein said reaction section contains one or more acidic zeolite catalysts.

12. A process according to claim 1, wherein said reaction section contains one or more acidic zeolite catalysts selected from the group consisting of: zeolite beta, zeolite Y, ZSM-5, ZSM-12, MCM-22, MCM-36, MCM-49, MCM-56, MCM-58, MCM-68, Faujasite, Mordenite, zirconium phosphate, and porous crystalline magnesium silicates.

13. A process for production of desired alkyl aromatic compound(s) from an aromatic feedstock and an olefin feedstock utilizing acidic zeolite catalyst(s) wherein:
   (a) the olefin feedstock is pretreated to remove or substantially reduce nitrogen compound(s) that can lead to deactivation of the acidic zeolite catalyst(s) used in the reaction section of the plant utilizing a distillation step to remove said nitrogen compounds from the olefin feedstock, wherein said nitrogen compound(s) comprises at least one of n-formyl morpholine, n-methylpyrrolidinone and ammonia;
   (b) the treated olefin feedstock is then reacted with the aromatic feedstock in the reaction section to produce the desired alkyl aromatic compound(s); and,
   (c) a distillation section is used to isolate the desired alkyl aromatic compound(s), recycle unreacted feedstock and recoverable byproducts, and purge unrecoverable byproducts.

14. A process according to claim 13, wherein the feedstock is pretreated as it enters the process, together with pretreatment and/or purification steps other than distillation, or after pretreatment and/or purification steps other than distillation, but prior to entering the reaction section.

15. A process according to claim 14, wherein said feedstock is pretreated together with at least one other stream in the process or after it is pretreated and/or purified together with the other stream in the process by said other pretreatment and/or purification steps.

16. A process according to claim 13, wherein at least one feedstock pretreatment includes at least a distillation step.

17. A process according to claim 13, wherein at least one feedstock pretreatment includes at least a distillation step, in which at least one nitrogen contaminant is removed at or near the top of a distillation column and the pretreated feedstock is recovered at or near the bottom of the column.

18. A process according to claim 13, wherein at least one feedstock pretreatment includes at least a distillation step, in which at least one nitrogen contaminant is removed at or near the bottom of a distillation column and the pretreated feedstock is recovered at or near the top of the column.

19. A process according to claim 13, wherein at least one feedstock pretreatment includes at least a distillation step, in which at least one nitrogen compound that is lighter relative to the olefin feedstock and/or other impurities that are lighter relative to the olefin feedstock are removed at or near the top of a distillation column, at least a nitrogen compound that is heavier relative to the olefin feedstock and/or other impurities that are heavier relative to olefin feedstock are removed at or near the bottom of the distillation column, and the pretreated olefin feed is recovered as a side draw.

20. A process according to claim 13, wherein said olefin feedstock contains olefins having 2 to 4 carbon atoms.

21. A process according to claim 13, wherein said olefin feedstock is selected from the group consisting of ethylene, propylene, 1-butene, cis-2-butene, trans-2-butene, isobutene, and mixtures thereof.

22. A process according to claim 13, wherein said desired alkyl aromatic compound(s) comprise of at least one selected from the group consisting of ethylbenzene, cumene, n-propyl benzene, butylbenzenes, diethylbenzenes, diisopropylbenzenes, dibutylbenzenes, ethyltoluenes, cymenes, butyltoluenes, ethylcumenes, butyl ethylbenzenes, butylcumenes, and mixtures thereof.

23. A process according to claim 13, wherein said desired alkyl aromatic compound(s) comprise of at least one selected from the group consisting of ethylbenzene, cumene, diethylbenzene isomer mixture, para-diethylbenzene, meta-diethylbenzene, diisopropylbenzene isomer mixture, para-diisopropylbenzene, meta-diisopropylbenzene, and mixtures thereof.

24. A process according to claim 13, wherein said reaction section contains one or more acidic zeolite catalysts.

25. A process according to claim 13, wherein said reaction section contains one or more acidic zeolite catalysts selected from the group consisting of zeolite beta, zeolite Y, ZSM-5, ZSM-12, MCM-22, MCM-36, MCM-49, MCM-56, MCM-58, MCM-68, Faujasite, Mordenite, zirconium phosphate, and porous crystalline magnesium silicates.

* * * * *